(12) United States Patent
Tan-Malecki et al.

(10) Patent No.: US 9,980,806 B2
(45) Date of Patent: May 29, 2018

(54) SHAPE MEMORY TUBULAR STENT WITH GROOVES

(71) Applicant: BOSTON SCIENTIFIC SCIMED, INC., Maple Grove, MN (US)

(72) Inventors: Francisca Tan-Malecki, Westlake Village, CA (US); Claude O. Clerc, Marlborough, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days. days.

(21) Appl. No.: 15/040,373

(22) Filed: Feb. 10, 2016

(65) Prior Publication Data

US 2016/0157991 A1     Jun. 9, 2016

Related U.S. Application Data

(63) Continuation of application No. 12/580,565, filed on Oct. 16, 2009, now abandoned.

(60) Provisional application No. 61/107,440, filed on Oct. 22, 2008.

(51) Int. Cl.
| | | |
|---|---|---|
| *A61F 2/07* | (2013.01) | |
| *A61F 2/94* | (2013.01) | |
| *A61F 2/844* | (2013.01) | |
| *A61F 2/848* | (2013.01) | |
| *A61F 2/89* | (2013.01) | |
| *A61F 2/958* | (2013.01) | |
| *A61F 2/04* | (2013.01) | |

(52) U.S. Cl.
CPC ............... *A61F 2/07* (2013.01); *A61F 2/844* (2013.01); *A61F 2/848* (2013.01); *A61F 2/89* (2013.01); *A61F 2/94* (2013.01); *A61F 2/958* (2013.01); *A61F 2002/041* (2013.01); *A61F 2002/072* (2013.01); *A61F 2210/0014* (2013.01); *A61F 2230/0069* (2013.01); *A61F 2230/0091* (2013.01); *A61F 2250/0029* (2013.01); *A61F 2250/0036* (2013.01); *A61F 2250/0039* (2013.01)

(58) Field of Classification Search
CPC ...... A61F 2/04; A61F 2/07; A61F 2/84; A61F 2/844; A61F 2/89; A61F 2/94; A61F 2/958
See application file for complete search history.

(56) References Cited

U.S. PATENT DOCUMENTS

| | | |
|---|---|---|
| 2,127,903 A | 8/1938 | Bowen |
| 3,588,920 A | 6/1971 | Wesolowski |
| 3,938,529 A | 2/1976 | Gibbons |
| 4,164,045 A | 8/1979 | Bokros et al. |
| 4,307,723 A | 12/1981 | Finney |
| 4,790,810 A | 12/1988 | Pugh, Jr. et al. |
| 4,813,925 A | 3/1989 | Anderson, Jr. et al. |
| 4,846,791 A | 7/1989 | Nattier et al. |

(Continued)

FOREIGN PATENT DOCUMENTS

| | | |
|---|---|---|
| WO | 2006062957 A1 | 6/2006 |
| WO | 2007020110 A1 | 2/2007 |
| WO | 2007149184 A1 | 12/2007 |

*Primary Examiner* — Alvin Stewart
(74) *Attorney, Agent, or Firm* — Seager, Tufte & Wickhem, LLP

(57) ABSTRACT

An implantable, radially distensible stent includes a tubular structure having opposed open ends. The wall of the stent is made from a shape memory polymeric material. Grooves may be disposed within an outer surface of stent wall to improve flexibility and drainage of the stent.

20 Claims, 8 Drawing Sheets

(56) References Cited

U.S. PATENT DOCUMENTS

| | | |
|---|---|---|
| 4,957,508 A | 9/1990 | Kaneko et al. |
| 5,108,416 A | 4/1992 | Ryan et al. |
| 5,129,405 A | 7/1992 | Milijasevic et al. |
| 5,129,910 A | 7/1992 | Phan et al. |
| 5,163,952 A | 11/1992 | Froix |
| 5,176,626 A | 1/1993 | Soehendra |
| 5,180,392 A | 1/1993 | Skeie et al. |
| 5,191,883 A | 3/1993 | Lennox et al. |
| 5,273,053 A | 12/1993 | Pohndorf |
| 5,306,300 A | 4/1994 | Berry |
| 5,366,506 A | 11/1994 | Davis |
| 5,383,927 A | 1/1995 | De Goicoechea et al. |
| 5,425,764 A | 6/1995 | Fournier et al. |
| 5,441,515 A | 8/1995 | Khosravi et al. |
| 5,531,741 A | 7/1996 | Barbacci |
| 5,599,291 A | 2/1997 | Balbierz et al. |
| 5,603,722 A | 2/1997 | Phan et al. |
| 5,607,464 A | 3/1997 | Trescony et al. |
| 5,628,780 A | 5/1997 | Helland et al. |
| 5,647,843 A | 7/1997 | Mesrobian et al. |
| 5,681,274 A | 10/1997 | Perkins et al. |
| 5,697,970 A | 12/1997 | Schmitt et al. |
| 5,709,644 A | 1/1998 | Bush |
| 5,733,925 A | 3/1998 | Kunz et al. |
| 5,746,722 A | 5/1998 | Pohndorf et al. |
| 5,766,209 A | 6/1998 | Devonec |
| 5,776,160 A | 7/1998 | Pasricha et al. |
| 5,861,036 A | 1/1999 | Godin |
| 5,876,429 A | 3/1999 | Schroeppel |
| 5,984,965 A | 11/1999 | Knapp et al. |
| 5,989,207 A | 11/1999 | Hughes |
| 6,002,969 A | 12/1999 | Machek et al. |
| 6,022,602 A | 2/2000 | Nomura |
| 6,024,764 A | 2/2000 | Schroeppel |
| 6,071,307 A | 6/2000 | Rhee et al. |
| 6,090,117 A | 7/2000 | Shimizu |
| 6,090,996 A | 7/2000 | Li |
| 6,132,471 A | 10/2000 | Johlin, Jr. |
| 6,162,244 A | 12/2000 | Braun et al. |
| 6,168,619 B1 | 1/2001 | Dinh et al. |
| 6,200,335 B1 | 3/2001 | Igaki |
| 6,214,037 B1 | 4/2001 | Mitchell et al. |
| 6,221,060 B1 | 4/2001 | Willard |
| 6,258,117 B1 | 7/2001 | Camrud et al. |
| 6,273,913 B1 | 8/2001 | Wright et al. |
| 6,312,462 B1 | 11/2001 | McDermott et al. |
| 6,358,275 B1 | 3/2002 | McIlroy et al. |
| 6,416,537 B1 | 7/2002 | Martakos et al. |
| 6,451,052 B1 | 9/2002 | Burmeister et al. |
| 6,468,312 B1 | 10/2002 | Rennebeck et al. |
| 6,517,575 B1 | 2/2003 | Yang et al. |
| 6,562,066 B1 | 5/2003 | Martin |
| 6,579,305 B1 | 6/2003 | Lashinski |
| 6,585,764 B2 | 7/2003 | Wright et al. |
| 6,626,936 B2 | 9/2003 | Stinson |
| 6,699,281 B2 | 3/2004 | Vallana et al. |
| 6,709,451 B1 | 3/2004 | Noble et al. |
| 6,709,455 B1 | 3/2004 | Chouinard |
| 6,712,845 B2 | 3/2004 | Hossainy |
| 6,716,242 B1 | 4/2004 | Altman |
| 6,719,804 B2 | 4/2004 | St. Pierre |
| 6,753,071 B1 | 6/2004 | Pacetti |
| 6,773,457 B2 | 8/2004 | Ivancev et al. |
| 6,808,536 B2 | 10/2004 | Wright et al. |
| 6,849,089 B2 | 2/2005 | Stoll |
| 6,866,805 B2 | 3/2005 | Hong et al. |
| 6,887,266 B2 | 5/2005 | Williams et al. |
| 6,921,390 B2 | 7/2005 | Bucay-Couto et al. |
| 6,926,724 B1 | 8/2005 | Chu |
| 6,926,735 B2 | 8/2005 | Henderson |
| 6,929,663 B2 | 8/2005 | Rioux et al. |
| 6,929,664 B2 | 8/2005 | Kolb |
| 6,949,118 B2 | 9/2005 | Kohler et al. |
| 6,985,777 B2 | 1/2006 | Tsuboi et al. |
| 7,082,337 B2 | 7/2006 | Sommer et al. |
| 7,090,693 B1 | 8/2006 | Chobotov et al. |
| 7,091,297 B2 | 8/2006 | Mather et al. |
| 7,115,691 B2 | 10/2006 | Alvarado et al. |
| 7,135,038 B1 | 11/2006 | Limon |
| 7,135,039 B2 | 11/2006 | De Scheerder et al. |
| 7,147,617 B2 | 12/2006 | Henderson et al. |
| 7,163,555 B2 | 1/2007 | Dinh |
| 7,169,178 B1 | 1/2007 | Santos et al. |
| 7,173,096 B2 | 2/2007 | Mather et al. |
| 7,175,644 B2 | 2/2007 | Cooper et al. |
| 7,179,289 B2 | 2/2007 | Shanley |
| 7,184,841 B1 | 2/2007 | Bodner et al. |
| 7,195,646 B2 | 3/2007 | Nahleili |
| 7,208,550 B2 | 4/2007 | Mather et al. |
| 7,211,114 B2 | 5/2007 | Bessler et al. |
| 7,218,972 B2 | 5/2007 | Rodriguez |
| 7,261,735 B2 | 8/2007 | Llanos et al. |
| RE39,923 E | 11/2007 | Blom |
| 7,329,286 B2 | 2/2008 | Raphael et al. |
| 7,338,530 B2 | 3/2008 | Carter et al. |
| 7,344,563 B2 | 3/2008 | Vallana et al. |
| 7,344,566 B2 | 3/2008 | Raphael et al. |
| RE40,404 E | 6/2008 | Schmitt et al. |
| 7,384,660 B2 | 6/2008 | Hossainy et al. |
| 7,402,172 B2 | 7/2008 | Chin et al. |
| 7,485,151 B2 | 2/2009 | Reever |
| 7,513,914 B2 | 4/2009 | Schurr |
| 7,618,398 B2 | 11/2009 | Holman et al. |
| 7,727,271 B2 | 6/2010 | Kujawski et al. |
| 7,731,757 B2 | 6/2010 | Taylor et al. |
| 7,785,365 B2 | 8/2010 | Holman et al. |
| 7,794,494 B2 | 9/2010 | Sahatjian et al. |
| 7,806,922 B2 | 10/2010 | Henderson et al. |
| 7,842,098 B2 | 11/2010 | Rioux et al. |
| 7,887,578 B2 | 2/2011 | Schneider |
| 7,909,799 B2 | 3/2011 | Frassica |
| 7,914,639 B2 | 3/2011 | Layne et al. |
| 7,918,885 B2 | 4/2011 | Sievers et al. |
| 7,935,131 B2 | 5/2011 | Anthamatten et al. |
| 7,938,855 B2 | 5/2011 | Gregorich et al. |
| 7,955,382 B2 | 6/2011 | Flanagan et al. |
| 7,981,162 B2 | 7/2011 | Stack et al. |
| 7,993,390 B2 | 8/2011 | Miller et al. |
| 8,007,702 B2 | 8/2011 | Gellman |
| 8,034,046 B2 | 10/2011 | Eidenschink |
| 8,118,855 B2 | 2/2012 | Hartley et al. |
| 2001/0041929 A1 | 11/2001 | Oepen |
| 2001/0051766 A1 | 12/2001 | Gazdzinski |
| 2002/0151968 A1 | 10/2002 | Zilla et al. |
| 2003/0018306 A1 | 1/2003 | Bucay-Couto et al. |
| 2003/0033004 A1 | 2/2003 | Ishii et al. |
| 2003/0055198 A1 | 3/2003 | Langer et al. |
| 2003/0093145 A1 | 5/2003 | Lawrence-Brown et al. |
| 2003/0100859 A1 | 5/2003 | Henderson et al. |
| 2003/0149488 A1 | 8/2003 | Metzger et al. |
| 2003/0153983 A1 | 8/2003 | Miller et al. |
| 2003/0190406 A1 | 10/2003 | Hossainy et al. |
| 2003/0208279 A1 | 11/2003 | Atala |
| 2003/0216803 A1 | 11/2003 | Ledergerber |
| 2003/0229392 A1 | 12/2003 | Wong |
| 2004/0019375 A1 | 1/2004 | Casey, II et al. |
| 2004/0034403 A1 | 2/2004 | Schmitt |
| 2004/0117031 A1 | 6/2004 | Stack et al. |
| 2004/0122526 A1 | 6/2004 | Imran |
| 2004/0127996 A1 | 7/2004 | Reever |
| 2004/0193283 A1 | 9/2004 | Rioux et al. |
| 2004/0249436 A1 | 12/2004 | Aznoian et al. |
| 2004/0260386 A1 | 12/2004 | Shalaby |
| 2005/0010275 A1 | 1/2005 | Sahatjian et al. |
| 2005/0043751 A1 | 2/2005 | Phan et al. |
| 2005/0049718 A1 | 3/2005 | Dann et al. |
| 2005/0070996 A1 | 3/2005 | Dinh et al. |
| 2005/0165366 A1 | 7/2005 | Brustad et al. |
| 2005/0216074 A1 | 9/2005 | Sahatjian et al. |
| 2005/0240278 A1 | 10/2005 | Aliski et al. |
| 2005/0245719 A1 | 11/2005 | Mather et al. |
| 2005/0251249 A1 | 11/2005 | Sashatjian et al. |
| 2006/0079957 A1 | 4/2006 | Chin et al. |
| 2007/0135578 A1 | 6/2007 | Mather et al. |

(56) References Cited

U.S. PATENT DOCUMENTS

| | | |
|---|---|---|
| 2007/0142562 A1 | 6/2007 | Mather et al. |
| 2007/0156228 A1 | 7/2007 | Majercak et al. |
| 2007/0215268 A1 | 9/2007 | Pingleton et al. |
| 2008/0001333 A1 | 1/2008 | Kleine et al. |
| 2008/0071353 A1 | 3/2008 | Weber et al. |
| 2008/0086201 A1 | 4/2008 | Weber et al. |
| 2008/0086214 A1 | 4/2008 | Hardin et al. |
| 2008/0097349 A1 | 4/2008 | Dillinger |
| 2008/0228262 A1 | 9/2008 | Goldmann et al. |
| 2008/0234719 A1 | 9/2008 | Adams |
| 2008/0243140 A1 | 10/2008 | Gopferich et al. |
| 2008/0319540 A1 | 12/2008 | Jordan et al. |
| 2009/0030363 A1 | 1/2009 | Gellman |
| 2009/0062927 A1 | 3/2009 | Marten et al. |
| 2009/0125058 A1 | 5/2009 | Bodner et al. |
| 2009/0125118 A1 | 5/2009 | Gong |
| 2009/0216337 A1 | 8/2009 | Egan et al. |
| 2009/0297635 A1 | 12/2009 | Sheth |
| 2009/0299488 A1 | 12/2009 | Devonec |
| 2010/0100105 A1 | 4/2010 | Bates et al. |
| 2010/0174381 A1 | 7/2010 | Benz et al. |
| 2010/0211181 A1 | 8/2010 | Prabhu et al. |
| 2010/0286794 A1 | 11/2010 | Ferreyrol |
| 2010/0319836 A1 | 12/2010 | Blank et al. |
| 2011/0005661 A1 | 1/2011 | Brustad et al. |
| 2011/0196507 A1 | 8/2011 | St. Pierre |

SHAPE MEMORY TUBULAR STENT WITH GROOVES

CROSS-REFERENCE TO RELATED APPLICATIONS

This application is continuation of U.S. application Ser. No. 12/580,565, filed Oct. 16, 2009, which claims the benefit of U.S. Provisional Application No. 61/107,440, filed Oct. 22, 2008, the contents of which are incorporated herein by reference.

FIELD OF THE INVENTION

This invention relates to a polymeric stent. More particularly, the invention relates to a shape memory polymeric stent having grooves.

BACKGROUND OF THE INVENTION

An intraluminary prosthesis is a medical device used in the treatment of diseased bodily lumens. One type of intraluminary prosthesis used in the repair and/or treatment of diseases in various body vessels is a stent. A stent is generally a longitudinal tubular device formed of biocompatible material which is useful to open and support various lumens in the body. For example, stents may be used in the bodily vessel, such as in the coronary or peripheral vasculature, esophagus, trachea, bronchi colon, biliary tract, urinary tract, prostate, brain, as well as in a variety of other applications in the body. These devices are implanted within the vessel to open and/or reinforce collapsing or partially occluded sections of the lumen.

While stents are often made from metallic materials, the use of plastic stents is not uncommon, especially in non-vascular applications. For example, plastic stents have been used to treat malignant or benign strictures throughout the gastrointestinal tract because of, among other things, ease of placement and non-permanency of the stents. Benign strictures in biliary applications are often treated every three months with a plastic stent for up to about a year. Rigid plastic tubes were also used to treat esophageal strictures, but have been replaced by self-expanding stents.

Each year many patients are diagnosed with malignant biliary disease. Other diagnosis include benign disease, post-surgical and questionable malignant. Typically, a patient with biliary disease presents symptoms such as jaundice, weight loss, abdominal pain, and back pain. These patients often suffer from an obstruction in the pancreaticobiliary ductal system. Numerous diseases can cause the inability of bile flow, however, the presence of gallstones and/or strictures is the most prevalent. For benign strictures, stenting or cathetering may be a useful resolution. Some stents or catheters, however, commonly get blocked and clog up. The patient often returns for another stent or catheter, where the physician often does not remove the previous stent or catheter and simply inserts another stent or catheter. Patients with benign strictures often have 4 to 5 stent or catheter packed into their common bile ducts. Usually, bile ducts can remodel, but 20% don't after multiple stent or catheter insertions.

Such plastic stents or catheters may have fairly thick walls. Such thick walls may make delivery through curved lumens difficult. Further, such thick walled devices may not be flexible.

Thus, there is a need for a polymeric stent which has improved patency by reducing re-intervention rates due, for example, to tumor in-growth, while still being flexible so that it can used in curved lumens.

SUMMARY OF THE INVENTION

In one embodiment, the present invention is directed to a shape memory stent. The shape memory tubular stent has applications in bodily lumens, such as but not limited to the common bile duct, pancreatic duct and hepatic ducts where a solid stent is needed and where in-growth can occur due to proliferating oncologous cells. The shape memory tubular stent may further include grooves into its outer surface to increase flexibility of the stent. Having grooves on the outside surface of the stent may also decrease pancreatitis and prevent migration. The grooves may allow the secretion of bile from other bifurcating ducts (pancreatic and hylar ducts) over the outside of the stent. The grooves may also allow some cellular in-growth on the outside of the stent. The stent may be a solid tube without substantial openings for the prevention of cellular in-growth. Decreasing pancreatitis by not blocking flow from the bifurcating ducts of the common bile duct may also be accomplished by placing small holes into the stent. The holes may be distant for each other to decrease cellular in-growth.

In one embodiment, the invention is directed to an implantable, radially distensible device or stent comprising a tubular structure having an open first end and an opposed open second end, the tubular structure having a wall between said first open end and said second end to define an open lumen therethrough, the wall having an outer surface and an opposed inner surface defining a wall thickness therebetween; the wall comprising a polymeric material; and grooves disposed within the outer surface of said wall; wherein the tubular structure is a self-supporting wall structure. The stent may be radially distensible between a radially contracted state and a radially expanded state. Desirably, the self-supporting wall structure does not have an open lattice wall structure or gaps in both radially contracted and radially expanded states. Further, the stent wall may be self-supporting without other support structure incorporated into or abutting the tubular structure.

The grooves may be present in the wall when the stent is in a radially contracted state, in a radially expanded state. The shape of the grooves may include or comprise a semicircular groove, a truncated circular groove, a semicircular groove with rounded surfaces, a groove having a flat bottom portion and smoothly rounded sides, a triangular-shaped groove, a groove having a flat bottom portion and sloped sides, a square-shaped groove, a rectangular-shaped groove, and combinations thereof. The grooves may be a plurality of radially orientated grooves, a plurality of helically orientated grooves, a plurality of interconnected grooves, including interconnected helically orientated grooves having a first helical pattern and a second helical pattern, such as crisscrossed helical grooves, and combinations thereof.

The polymeric material of the stent wall may comprise shape memory polymer. A useful polymeric material of the stent wall may comprise shape memory polymeric polycyclooctene. The polymeric material of the stent wall may further include a radiopaque material.

In another embodiment an open lattice stent wall structure of shape memory polymeric material is provided. The open lattice wall structure may be contiguous or may include spaced apart stent members. A graft may be disposed over the stent wall structure, may be disposed in between the open spaces within the stent wall structure, or may embed or surround the stent wall structure, or otherwise simply engage the stent structure. The graft may be made from a material that is different from the shape memory polymeric material of the open lattice stent wall structure to provide a composite implantable device or stent-graft.

In another embodiment, the invention is directed to a method of making a stent. The method may comprise the steps of providing a shape memory polymer; forming the shape memory polymer into a tubular structure having an open first end and an opposed open second end, the tubular structure having a wall between said first open end and said second end to define an open lumen therethrough, the wall having an outer surface and an opposed inner surface defining a wall thickness therebetween; and disposing grooves within the outer surface of the wall. The step of providing the shape memory polymer may further comprise providing shape memory polymeric polycyclooctene. The step of forming the shape memory polymer into the tubular structure may further comprise molding the shape memory polymer, casting the shape memory polymer, and/or extruding the shape memory polymer. The step of disposing grooves within the inner surface of the wall may further comprise mechanically forming the grooves, such as by milling, grinding, cutting, laser cutting, masking and/or etching the outer surface of the wall to form the grooves; and/or step of disposing grooves within the outer surface of the wall may further comprise molding the grooves and/or removing a sacrificial layer or filament to so form the grooves.

In another embodiment, the invention is directed to an assembly for intraluminal delivery of a stent. The assembly may comprise a delivery device having an elongate tube; and a radially distensible stent comprising a tubular structure having an open first end and an opposed open second end, the tubular structure having a wall between said first open end and said second end to define an open lumen therethrough, the wall having an outer surface and an opposed inner surface defining a wall thickness therebetween; the wall comprising a shape memory polymeric material; and grooves disposed within the outer surface of said wall; wherein the stent is disposed in a contracted state on the elongate tube of the delivery device. The delivery device may further comprise an expandable balloon or other mechanical expanding device, a heat source, and combinations thereof In another embodiment, the invention is directed to a method for intraluminal delivery of a stent. The method may comprise the steps of providing an assembly, which may comprise a delivery device having an elongate tube; and a radially distensible stent comprising a tubular structure having at least an open first end and an opposed open second end, the tubular structure having a wall between said first open end and said second end to define an open lumen therethrough, the wall having an outer surface and an opposed inner surface defining a wall thickness therebetween; the wall comprising a shape memory polymeric material; and grooves disposed within the outer surface of said wall; wherein the stent is disposed in a contracted state on the elongate tube of the delivery device; advancing the assembly to a site within a bodily lumen; radially expanding the stent within the bodily lumen; and withdrawing the delivery device to leave the stent within the bodily lumen. Further, the stent of the present invention may comprise multiple openings and/or multiple lumens.

Moreover, the structure of the present invention may comprise a shape memory polymer and other material. For example, shape memory polymer may be layered over a flexible graft or stent which may comprise a different material from the shape memory material or may comprise a similar or the same material as from the shape memory material. The other material may also be shape memory, including polymeric materials and non-polymeric materials, for example metallic shape memory materials.

These and other embodiments, objectives, aspects, features and advantages of this invention will become apparent from the following detailed description of illustrative embodiments thereof, which is to be read in connection with the accompanying drawings in which like reference characters refer to the same parts or elements throughout the different views. The drawings are not necessarily to scale, emphasis instead being placed upon illustrating the principles of the invention.

DETAILED DESCRIPTION OF THE INVENTION

Figure 1:
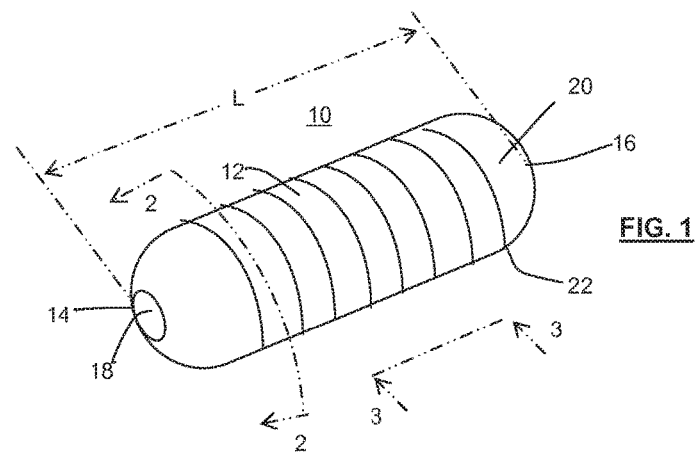
FIG. 1 is a perspective view of a stent according to the present invention.

FIG. 1 illustrates a perspective view of an implantable, radially distensible device or stent 10 of the present invention. Stent 10 is a tubular structure having a wall 12 and opposed open ends 14, 16, defining an open lumen 18 therebetween. The length, L, of the stent may vary from about 1 cm (or about 0.4 inches) to about 15 cm (or about 6 inches). Such lengths are non-limiting, and the stent 10 may have any suitable length for its intended purpose. The stent 10 may further include a plurality of grooves 22 disposed within the outer surface 20 of the stent 10. The grooves 22 may be fully or partially circumferential. The ends 14, 16 may be rounded or smooth to facilitate delivery of the stent 10 within a bodily lumen (not shown) and/or to provide for smooth flow of a bodily fluid (not shown) at the ends 14, 16 and/or through open lumen 18. Further, the edge of the ends 14, 16 that are proximal to the open lumen 18 may also be rounded and/or may be curved inward, i.e., concavely shaped as depicted in FIG. 3.

Figure 2:
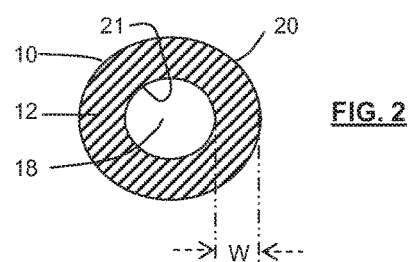
FIG. 2 is a cross-section view of the stent of FIG. 1 taken along the 2-2 axis.

FIG. 2 illustrates a cross-sectional view of the stent 10 of FIG. 1 taken along the 2-2 axis. The stent wall 12 includes an outer surface 20 and an inner surface 21. The inner surface 21 of the stent wall 12 may also define the open lumen 18 of the stent 10. The stent wall 12 depicted in FIG. 2 is a substantially solid tubular wall, i.e., free and/or substantially free of an open lattice structure having gaps in the wall. In one embodiment, the stent wall 12 is a unitary structure, which may suitably be formed by molding, casting, extruding, and the like, as contrasted to a non-unitary structure, such as a stent wall formed from a plurality of elongate filaments. The thickness, W, of the stent wall 12 may vary. In the same or different embodiment, the thickness of the stent wall 12 is selected, in part, to provide a self-supporting tubular structure. The thickness, W, may vary from about 0.038 cm (or about 0.015 inches) to about 0.635 cm (or about 0.25 inches). These wall thicknesses are non-limiting, and any suitable wall thickness may be used.

Figure 3:
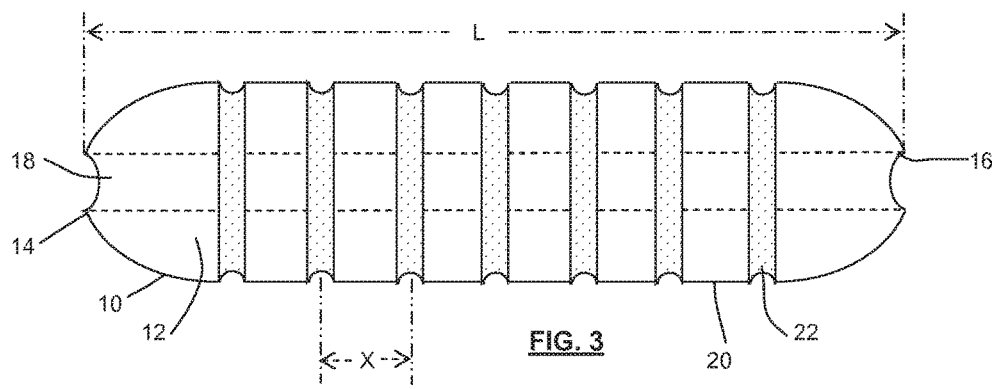
FIG. 3 is a side elevational view of the stent of FIG. 1 taken along the 3-3 axis showing radial grooves disposed on the outer surface of the stent.

FIG. 3 illustrates a side elevational view of the stent 10 of FIG. 1, taken along the 3-3 axis. The stent 10 may include a series or plurality of radially or circumferentially disposed grooves 22. Desirably, the grooves 22 are disposed at a frequency or spacing along the longitudinal length, L, of the stent 10. For example, grooves 22 may be disposed at a length X between juxtaposed grooves 22. For example, X may vary from about 0.25 cm (or about 0.1 inches) to about 3 cm (or about 1.2 inches). These frequencies or spacings are non-limiting, and any desirable frequency or spacing may suitably be used. Further, the frequency or spacing of the grooves 22 may be regular, equal, substantially equal and/or somewhat equal along the longitudinal L of the stent 10. The present invention, however, is not so limited. For example, only portions of the longitudinal expanse of the stent 10 may have a frequency or spacing of grooves 22 while other longitudinal portions of the stent 10 may be free of such grooves (not shown). Further, the grooves 22 may also be disposed over and into the surface of the stent 10 in irregular pattern (not shown). Further, the grooves 22 may be fully or partially circumferential. Moreover, the grooves 22 may have any suitable geometry, such as but not limited to semi-circular, angular, semi-polygonal and the like. The grooves 22 in the stent 12 may be formed directly during the molding or casting of the stent 10. Alternatively, or in addition to, the grooves 22 may be machined into the stent wall 12 by, for example but not limited to, milling, grinding, cutting, laser cutting, etching and the like. Moreover the grooves 22 may be formed masking or by the use of a sacrificial layer or filament.

Figure 4:
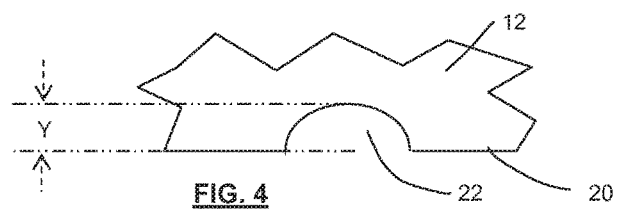
FIG. 4 is an exploded view of a portion of the stent of FIG. 4.

FIG. 4 is an exploded view of a portion of the stent wall 12 of FIG. 3. The groove 22 may have a depth Y. Desirably, the depth Y of the groove 22 into the stent wall 12, as measured from the outer surface 20 of the stent wall 12, may vary from about 5 percent of the wall thickness to about 50 percent of the wall thickness W. Such depths of the grooves 22 are nonlimiting, and any desired depth may suitably be used. Desirably, the depth Y does not completely traverse the wall thickness W.

Figure 5:
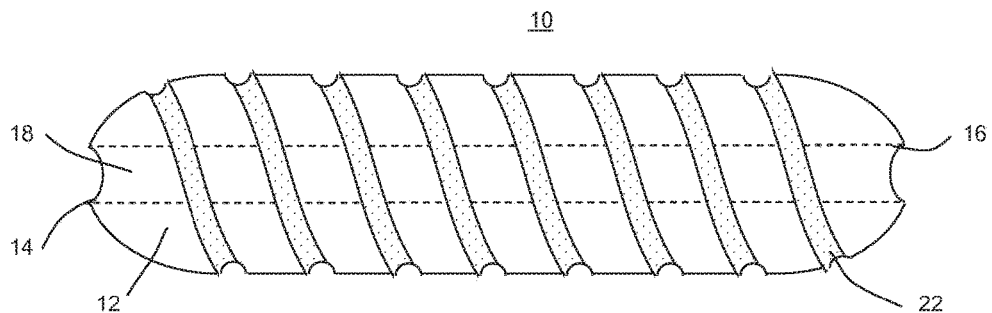
FIG. 5 depicts an alternate embodiment of the stent of FIG. 3 showing helical grooves disposed on the outer surface of the stent.
Figure 6:
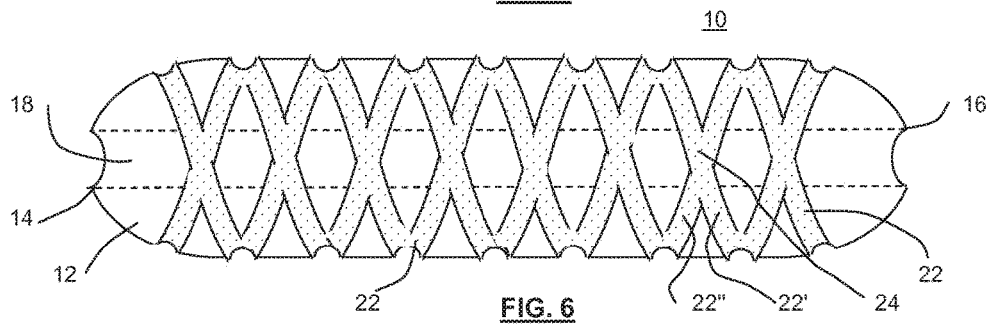
FIG. 6 depicts an alternate embodiment of the stent of FIG. 3 showing helically crisscrossing grooves disposed on the outer surface of the stent.

FIGS. 5 and 6 depict additional arrangements of the grooves 22 within the outer surface 20 of the stent 10 of the present invention. As depicted in FIG. 5, the grooves 22 may be helically disposed about the stent 10. As depicted in FIG. 6, the grooves 22 may be crisscrossed helical grooves 22. For example, groove 22' and groove 22" may have different helical orientations, for example approximately opposite helical orientations. The grooves 22' and 22" may intersect at grooved portion 24. The present invention, however, is not so limited and any useful regular or irregular pattern of grooves may suitably be used.

Figure 7:
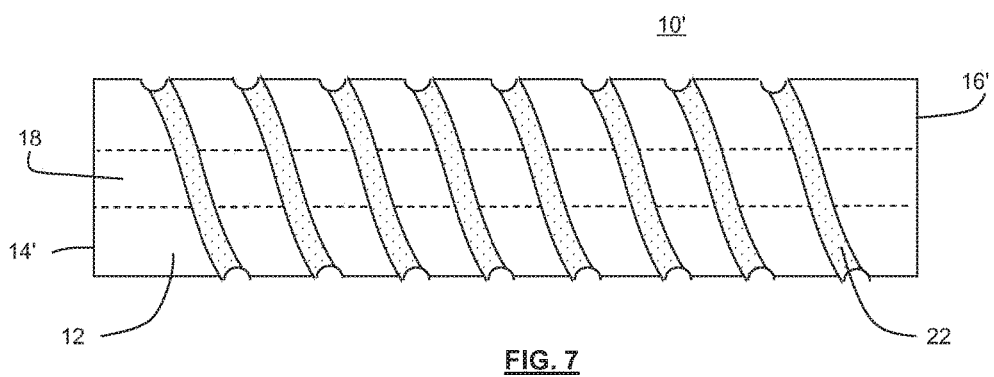
FIG. 7 depicts an alternate embodiment of the stent of FIG. 1 showing a stent with non-rounded stent ends.
Figure 8:
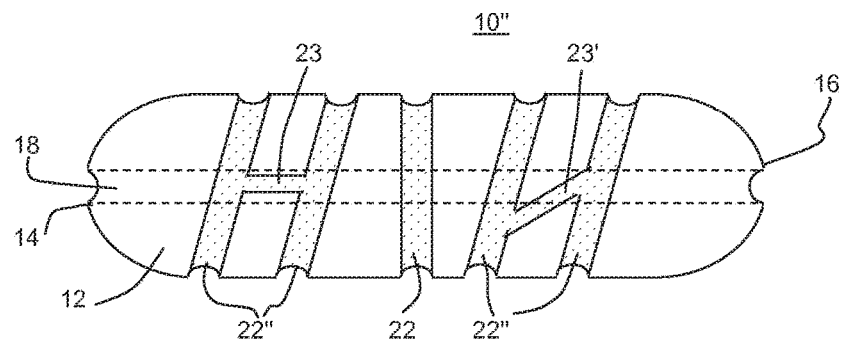
FIG. 8 depicts an alternate embodiment of the stent of FIG. 3 showing a stent with different inter-connected and non-interconnected grooves.

FIGS. 7 and 8 depict additional embodiments of the present invention. For example, the ends 14, 16 need not be rounded as depicted in FIGS. 1, 3, 5 and 6, and as depicted in FIG. 7 the ends 14' and 16' may be non-rounded or flat, including substantially flat and partially flat ends. Moreover, the stent 10 may have any further features or shapes useful for treatment within a bodily lumen, including flares, tapers, bumps, varying diameters, surface features, anchors and the like. One example of surface features include an outwardly extending geometric pattern which may serve as an anti-migration feature. Further details of stent having such anti-migration features, including stents of shape memory polymeric material, may be found in U.S. patent application Ser. No. 12/139,042, filed Jun. 13, 2008, which published as U.S. Patent Application Publication No. 2008/0319540 A1 on Dec. 25, 2008, the contents of which is incorporated herein by reference.

Further, as depicted in FIG. 8, grooves 22 may be interconnected by grooves 23, 23' which may have different orientations from the circumferential grooves 22 of FIG. 1 and the helical grooves 22 of FIG. 5. For example, groove 23 may be a longitudinal or substantially longitudinal groove, and groove 23' may be a helical interconnecting groove with a different helical orientation from helical grooves 22". Furthermore, as depicted in FIG. 8, the stent 10 of the present invention may include a combination arrangements of the circumferential grooves 22 and helical grooves 22". Thus, the stent 10 may include combinations of helical and non-helical grooves, which may be in part or total, interconnected or non-interconnected.

Figure 9A:
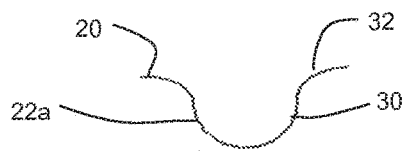
FIGS. 9A through 9E depict different shapes for the grooves on the surface of the stent.
Figure 9B:
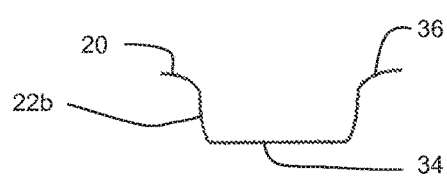
Figure 9C:
Figure 9D:
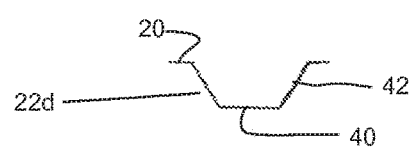
Figure 9E:

FIGS. 9A through 9E depict nonlimiting examples of additional suitable shapes of the grooves. For example, in addition to the semicircular or truncated circular groove 22 as depicted in FIG. 4, groove 22a, as depicted in FIG. 9A, may include a semicircular groove 30 with rounded surfaces 32 proximal to the outer surface 20 of the stent wall 12. As depicted in FIG. 9B, groove 22b may include a flat or somewhat flat bottom portion 34 and smooth, somewhat rounded, sides 36. As depicted in FIG. 9C, groove 22c may include a triangular shape 28. Further, as depicted in FIG. 9D, groove 22d may include a flat or somewhat flat bottom portion 40 and sloped sides 42. The groove 22d may be described as having a shape of a truncated hexagonal configuration. Moreover, as depicted in FIG. 9E, groove 22e may have a square shape 44 or even a rectangular shape (not shown). Further, any of the depicted shapes having sharp or pointed edges may be suitable be modified to include rounded and/or smooth edges. The stent 10 may include any of the grooves 22, 22a, 22b, 22c, 22d, 22e, as depicted or modified as described above, for example modified to include rounded or smooth edges, in total or in combination.

Figure 10:
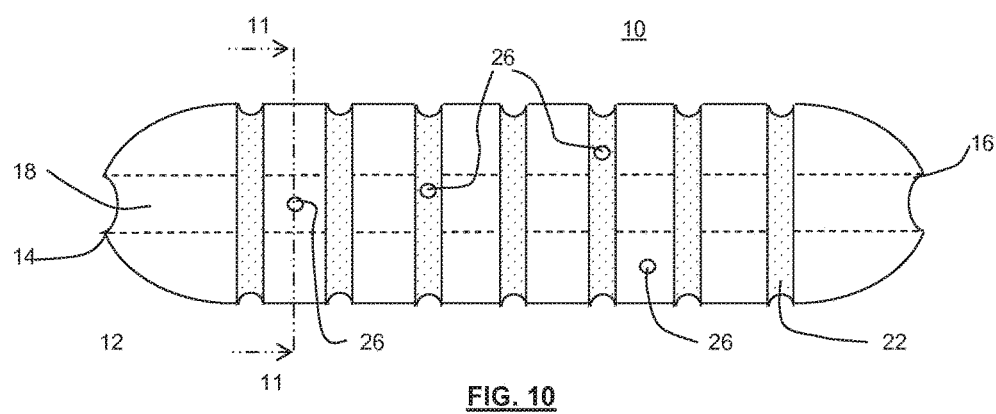
FIG. 10 depicts an alternate embodiment of the stent of FIG. 3 showing holes disposed on the stent.
Figure 11:
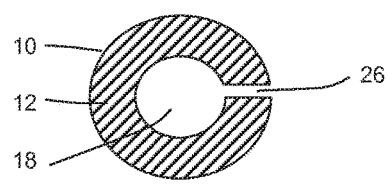
FIG. 11 is a cross-sectional view of the stent of FIG. 10 taken along the 11-11 axis depicting a hole through the stent wall.

As depicted in FIGS. 10 and 11, the stent 10 may include a hole 26 or a plurality of holes 26. The holes 26 may decrease pancreatitis by not blocking flow from bifurcating ducts of the common bile duct after the stent 10 has been so positioned. As depicted in FIG. 10, the holes 26 may be distant from one and the other to decrease then potential for or to inhibit cellular in-growth. The holes 26 may be disposed in any useful pattern, including regular repeating patterns and irregular patterns. As depicted in FIG. 11, the hole 26 may traverse through the stent wall 12. The holes may have any shape, for example but not limited to circular, slotted, polygonal and the like.

As described above, the stent 10 and the stent wall 12 desirably comprise, include or are made from shape memory polymers or shape memory polymeric materials. Shape memory refers to the ability of a material to undergo structural phase transformation such that the material may define a first configuration under particular physical and/or chemical conditions, and to revert to an alternate configuration upon a change in those conditions. Stimulus for such a phase transformation may include, but is not limited to, temperature, pH, salinity, hydration, pressure and others.

Shape memory polymers generally have hard segments and soft segments, which are relative terms relating to the transition temperature of the segments. As used herein, the term "segment" refers to a block or sequence of polymer forming part of the shape memory polymer. Generally speaking, hard segments have a higher glass transition temperature (Tg) than soft segments.

Useful natural polymer segments or polymers include, but are not limited to, proteins, such as casein, gelatin, gluten, zein, modified zein, serum albumin and collagen, polysaccharides, such as alginate, chitin, celluloses, dextrans, pullulane, and polyhyaluronic acid; poly(3-hydroxyalkanoate)s, poly(.beta.3-hydroxybutyrate), poly(3-hydroxyoctanoate) and poly(3-hydroxyfatty acids). Useful natural bioabsorbable or biodegradable polymer segments or polymers include polysaccharides such as alginate, dextran, cellulose, collagen and chemical derivatives thereof, and proteins such as albumin, zein and copolymers and blends thereof, alone or in combination with synthetic polymers. Suitable synthetic polymer blocks include polyphosphazenes, poly(vinyl alcohols), polyamides, polyester amides, poly(amino acid)s, synthetic poly(amino acids), polyanhydrides, polycarbonates, polyacrylates, polyalkylenes, polyacrylamides, polyalkylene glycols, polyalkylene oxides, polyalkylene terephthalates, polyortho esters, polyvinyl ethers, polyvinyl esters, polyvinyl halides, polyvinylpyrrolidone, polyesters, polylactides, polyglycolides, polysiloxanes, polyurethanes and copolymers thereof. Examples of suitable polyacrylates include poly(methyl methacrylate), poly(ethyl methacrylate), poly(butyl methacrylate), poly(isobutyl methacrylate), poly(hexyl methacrylate), poly(isodecyl methacrylate), poly (lauryl methacrylate), poly(phenyl methacrylate), poly(m-ethyl acrylate), poly(isopropyl acrylate), poly(isobutyl acrylate) and poly(octadecyl acrylate). Synthetically modified natural polymers include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, arboxymethyl cellulose, cellulose triacetate and cellulose sulfate sodium salt. Examples of synthetic biodegradable polymer segments or polymers include polyhydroxy acids, such as polylactides, polyglycolides and copolymers thereof; poly(ethylene terephthalate); poly(hydroxybutyric acid); poly(hydroxyvaleric acid); poly[lactide-co-(ε-caprolactone)]; poly[glycolide-co-(ε-caprolactone)]; polycarbonates, poly(pseudo amino acids); poly(amino acids); poly(hydroxyalkanoate)s; polyanhydrides; polyortho esters; and blends and copolymers thereof. Rapidly biodegradable polymers such as poly(lactide-co-glycolide)s, polyanhydrides, and polyorthoesters, which have carboxylic groups exposed on the external surface as the smooth surface of the polymer erodes, can also be used. In addition, polymers containing labile bonds, such as polyanhydrides and polyesters, are well known for their hydrolytic reactivity. Their hydrolytic degradation rates can generally be altered by simple changes in the polymer backbone and their sequence structure. Examples of suitable hydrophilic polymers include, but are not limited to, poly(ethylene oxide), polyvinyl pyrrolidone, polyvinyl alcohol, poly(ethylene glycol), polyacrylamide poly(hydroxy alkyl methacrylates), poly(hydroxy ethyl methacrylate), hydrophilic polyurethanes, poly(hydroxy ethyl acrylate), hydroxy ethyl cellulose, hydroxy propyl cellulose, methoxylated pectin gels, agar, starches, modified starches, alginates, hydroxy ethyl carbohydrates and mixtures and copolymers thereof. Hydrogels may also be suitably be used and can be formed from polyethylene glycol, polyethylene oxide, polyvinyl alcohol, polyvinyl pyrrolidone, polyacrylates, poly(ethylene terephthalate), poly(vinyl acetate), and copolymers and blends thereof. Several polymeric segments, for example, acrylic acid, are elastomeric only when the polymer is hydrated and hydrogels are formed. Other polymeric segments, for example, methacrylic acid, are crystalline and capable of phase transition even when the polymers are not hydrated. Either type of polymeric block can be used, depending on the desired application and conditions of use. Additional details of useful shape memory polymeric compositions may be found in U.S. Pat. No. 6,887,266 to Williams et al., the contents of which are incorporated herein by reference.

One useful class of useful shape memory polymers includes a class of (meth)acrylate compositions having a first (meth)acrylate monomer having a lower glass transition temperature (Tg), typically less than about 25° C., and a second (meth)acrylate monomer having a higher glass transition temperature (Tg), typically greater than about 25° C. These ranges of glass transition temperatures are, however, nonlimiting. Useful, but nonlimiting, first monomers include butyl (meth)acrylate, pentafluoropropylacrylate and combinations thereof. Useful, but nonlimiting, second monomers include methylmethacrylate, isobornyl methacrylate, isobutyl methacrylate, perfluoroacetylmethacrylate, tertiary butylmethacrylate, phenylethylmethacrylate, styrene, hydroxyethyl methacrylate, glycerol methacrylate, n-vinyl pyrrolidone, heptadecafluorodecyl methacrylate and combinations thereof. Such compositions may include a third of polyethyleneglycol dimethacrylate, polyethyleneglycol methacrylate, polyethyleneglycol acrylate and combinations thereof. Additional details of these compositions may be found in U.S. Pat. No. 7,115,691 to Alvarado et al., U.S. Pat. No. 5,603,722 to Phan et al. and U.S. Pat. No. 5,163,952 to Froix, the contents of which are incorporated herein by reference.

Other useful shape memory polymers include polynorbornene, polycaprolactone, polyenes, nylons, polycyclooctene (PCO), blends of PCO and styrene-butadiene rubber, polyvinyl acetate/polyvinylidinefluoride (PVAc/PVDF), blends of PVAc/PVDF/polymethylmethacrylate (PMMA), polyurethanes, styrene-butadiene copolymers, polyethylene (particularly, crosslinked polyethylene), transisoprene, block copolymers of polyethylene terephthalate (PET) and blends of polycaprolactone and n-butylacrylate. Desirably, the stent 10 or the stent wall 12 may comprise a shape memory polymer of polycyclooctene. Further details of such polycyclooctene shape memory polymers may be found in U.S. Pat. Nos. 7,091,297; 7,173,096 and 7,208,550 and in U.S. Patent Application Nos. 2005/0216074; 2005/0245719; 2005/0251249, 2007/0135578 and 2007/0142562, the contents of all of which are incorporated herein in their entirety by reference.

Suitable shape memory polymers for use with the stent 10 of the present invention may include elastomers that are typically crosslinked and/or crystalline and exhibit melt or glass transitions at temperatures that are above body temperature and safe for use in the body, e.g. at about 40° C. to about 50° C. Such suitable shape memory polymers include those that maintain stent geometry under expansion conditions where the stent 10 may be expanded without fracture or substantial irreversible stress relaxation or creep. Typically, the stent 10 may be heated to or above the melt or glass transition temperature of the shape memory polymer during expansion. In this condition, the polymer may be in a softened state. After the stent 10 is fully expanded and cooled, the shape memory polymer substantially sets in the proper apposition, e.g. about a bodily lumen. At the same time, the polymer can have some elastomeric properties in the cooled, hardened state so that the stent can flex with natural lumen motion. After cooling, the stent 10 should exhibit sufficient resistance to inward radial force of a body lumen wall so that the stent 10 keeps the body lumen open. The stent wall 12 should have sufficient strength, e.g., thickness and material selection for strength, so that the stent wall 12 can be kept relatively thin while still resisting lumen wall forces. The stent wall 12 may be made of mixtures and/or combinations polymers or multiple polymer layers.

Desirably, the stent 10 includes shape memory properties useful for delivery of the stent 10 within a bodily lumen. The shape memory polymer of the stent wall 12 can be configured to remember an enlarged or reduced diameter configuration. For example, the stent 10 can be delivered into the body in a contracted or radially reduced state, and then expanded by heat and/or radial pressure to a larger expanded state. If desired, the stent 10 may also be retrieved from a bodily lumen by reheating the stent 10 so that it returns to its contracted state, whereby it could then be removed and/or repositioned by a practitioner. In this case, heating causes the stent 10 to revert its smaller diameter condition, and accordingly the stent can be more easily removed from the bodily vessel as compared to stents not containing shape memory materials.

The stent 10 may be made by extruding or molding a suitable shape memory polymer and/or polymers to an initial diameter which may be about the same or greater than the diameter of a target lumen. The stent wall 12 may be machined, for example by any of the above-described methods, e.g., laser cutting, to provide a pattern of grooves 22 in a desirable geometric pattern. Alternatively, or in addition to, the pattern of grooves 22 may be formed into the stent wall surface 20 during molding of the stent wall 12. The shape memory polymer may then be recrystallized or crosslinked, if necessary. The stent 10 may be heated near or above the melt or glass transition and mechanically deformed to its smaller or contracted diameter, such as one suitable for delivery. The stent 10 may then be cooled, typically to room temperature. The stent 10 may be disposed onto a balloon catheter, delivered into the body, and expanded by application of heat to the melt or glass transition, while optionally inflating the balloon. As the polymer or polymers of the stent have shape memory properties, the stent 10 tends to expand upon heating to the larger, remembered diameter. At the transition temperature, shape memory polymers become malleable and elastic, thus allowing them to be expanded to sizes greater than 200%. A useful delivery catheter or endoscope may include a portion which may be heated or supply heat to expand the stent 10. The delivery catheter or endoscope may also include an inflatable balloon or other expander which may also be heated. The inflatable balloon and/or catheter or endoscope portion may include an electrically conductive fluid which may be heated by radiofrequency power. Such a delivery device is further described in U.S. Pat. No. 5,191,883, the contents of which are incorporated in their entirety by reference. Other methods may also be used to heat the stent 10 including circulating heated fluids, resistance heating, externally supplied heating, and the like.

Figure 12:
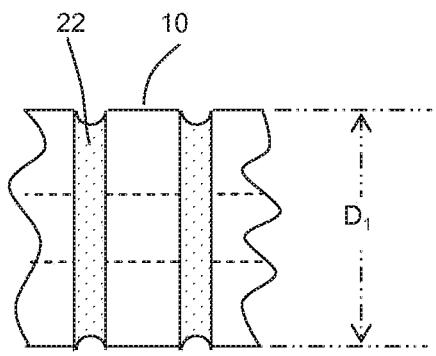
FIG. 12 is a partial view of the stent of FIG. 3 depicting the stent in a radially contracted state.
Figure 13:
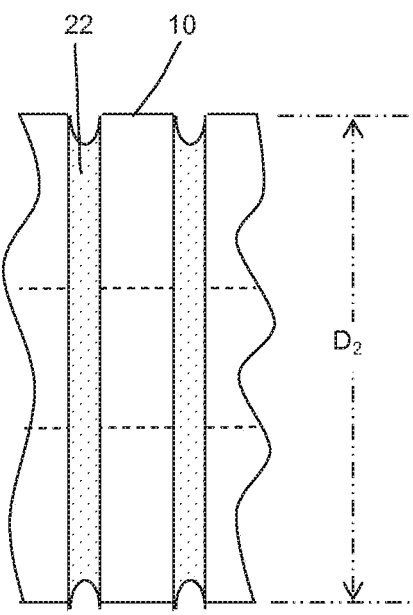
FIG. 13 is a partial view of the stent of FIG. 3 depicting the stent in a radially expanded state.

FIGS. 12 and 13 depict an exploded portion of the stent 10 of FIG. 3 in a radially contracted state and a radially expanded state, respectively. As depicted in FIGS. 12 and 13, stent 10 is radially distensible from a radially contracted state, as indicated by dimension $D_1$, to a radially expanded state, as indicated by dimension $D_2$, where $D_2$ is greater than $D_1$. For example, the stent 10 may have a contracted diameter D.sub.1 that is about 10 Fr (or about an outer diameter (OD) of about 3.3 mm). The stent 10 may be expanded to a larger diameter $D_2$, for example, from about 20 Fr (or about 6.7 mm OD) to about 30 Fr (or about 10 mm OD) or larger. Such diameters are nonlimiting, and the stent 10 may be formed and programmed to have any suitable contracted diameter $D_1$ and any suitable expanded diameter $D_2$.

Figure 14:
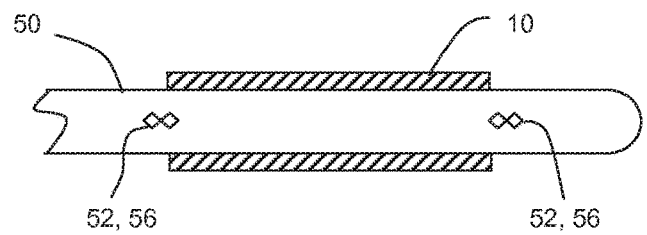
FIG. 14 is a schematic of the stent of FIG. 3 in a contracted state and being disposed over a delivery device.
Figure 15:
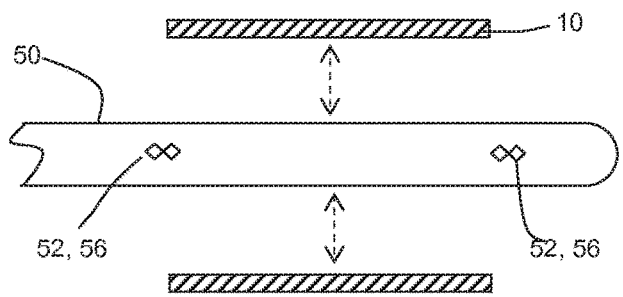
FIG. 15 is a schematic of the stent of FIG. 14 being radially expanded from the delivery device by action of heat.
Figure 16:
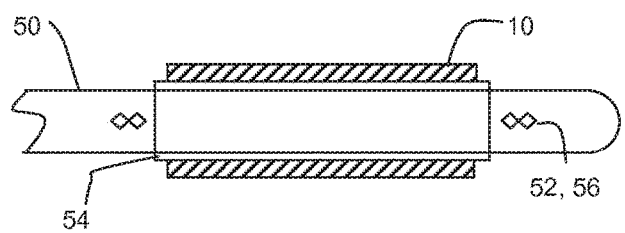
FIG. 16 is a schematic of the stent of FIG. 3 in a contracted state and being disposed over a delivery device having an expandable balloon.
Figure 17:
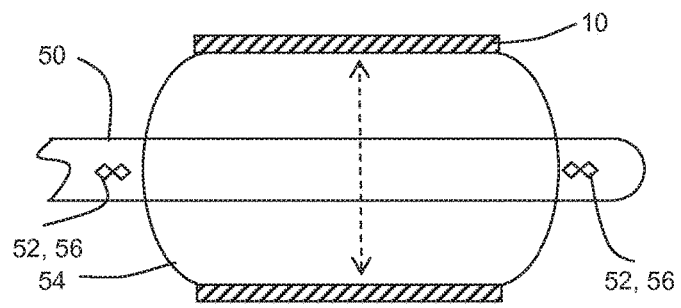
FIG. 17 is a schematic of the stent of FIG. 16 being radially expanded from the delivery device by action of pressure from expanding the balloon and/or by the application of heat.
Figure 18:
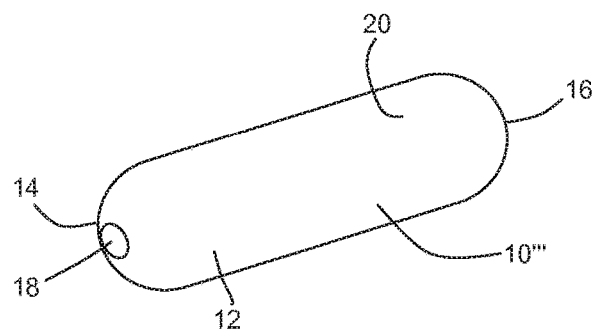
FIG. 18 depicts an alternate embodiment of the stent of FIG. 1 having no external grooves in its outer wall surface.

FIGS. 14 through 17 schematically depict delivery and/or delivery devices for the stent 10. As depicted in FIG. 14 stent 10 is in its contracted state, i.e., a non-limiting dimension of about 10 Fr (or about 3.3 mm OD) and is disposed over a delivery device 50, for example a catheter. The delivery device 50 may include a heat source 52. Any suitable heat source 52 may be used. In one embodiment, the heat source 52 may comprise electrodes 56. A conductive fluid, such as but not limited to saline (not shown), may be heated from energy supplied to the electrodes 56, for example by radio frequency (RF) energy (not shown). As depicted in FIG. 15, the stent 10 is distensible to its expanded state, i.e., from a non-limiting dimension of about 20 Fr (or about 6.7 mm OD) to a non-limiting dimension of about 30 Fr (or about 10 mm OD) or larger to be disposed within a bodily lumen (not shown). In general, a smaller delivery profile, e.g., contracted state, is preferred. The delivery device 50 may be withdrawn leaving the stent 10 behind and disposed within a bodily lumen (not shown). As depicted in FIGS. 16 and 17, the delivery device 50' may further include an expandable balloon 54. The use of the balloon 54 may aid the expansion of the stent 10 by applying an expansive force or pressure to the stent 10. Such expansive force may be used in addition to the above-described expansion by the application of heat. Further, the balloon 54 may also be filled with any suitable fluid, for example the conductive fluid or saline to further aid in the thermal expansion of the stent 10. The balloon 54 may be then deflated, and the delivery device 50' may be withdrawn leaving the stent 10 behind.

The stent 10 and the stent wall 12 may comprise radiopaque materials, such as metallic-based powders or ceramic-based powders, particulates or pastes which may be incorporated into the polymeric material. For example, the radiopaque material may be blended with the polymer composition from which the stent wall 12 is formed. Various radiopaque materials and their salts and derivatives may be used including, without limitation, bismuth, barium and its salts such as barium sulfate, tantalum, tungsten, gold, platinum and titanium, to name a few. Additional useful radiopaque materials may be found in U.S. Pat. No. 6,626,936, which is herein incorporated in its entirely by reference. Metallic complexes useful as radiopaque materials are also contemplated. The stent 10 may be selectively made radiopaque at desired areas along the stent or made be fully radiopaque, depending on the desired end-product and application. Alternatively, the stent 10 may also have improved external imaging under magnetic resonance imaging (MRI) and/or ultrasonic visualization techniques. MRI is produced by complex interactions of magnetic and radio frequency fields. Materials for enhancing MRI visibility include, but not be limited to, metal particles of gadolinium, iron, cobalt, nickel, dysprosium, dysprosium oxide, platinum, palladium, cobalt based alloys, iron based alloys, stainless steels, or other paramagnetic or ferromagnetic metals, gadolinium salts, gadolinium complexes, gadopentetate dimeglumine, compounds of copper, nickel, manganese, chromium, dysprosium and gadolinium. Moreover, the addition of heat-conductive materials like metals may further aid in heating or cooling the stent, including heating and/or cooling from an external source. To enhance the visibility under ultrasonic visualization the stent 10 of the present invention may include ultrasound resonant material, such as but not limited to gold. Other features, which may be included with the stent 10 of the present invention, include radiopaque markers; surface modification for ultrasound, therapeutic agent delivery; varying stiffness of the stent or stent components; varying geometry, such as tapering, flaring, bifurcation and the like; varying material; varying geometry of stent components, for example tapered stent ends; and the like.

The stent 10, 10', 10" of the present invention, however, is not limited to a tubular device having grooves on its external wall surface. As depicted in FIG. 11, stent 10''' may be a shape-memory polymeric stent having no or substantially no grooves on its external wall surface 20.

Figure 19:
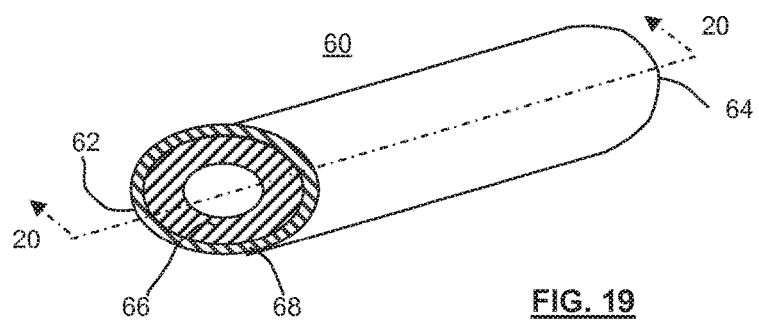
FIG. 19 depicts a stent-graft according to an alternate embodiment of the present invention.
Figure 20:
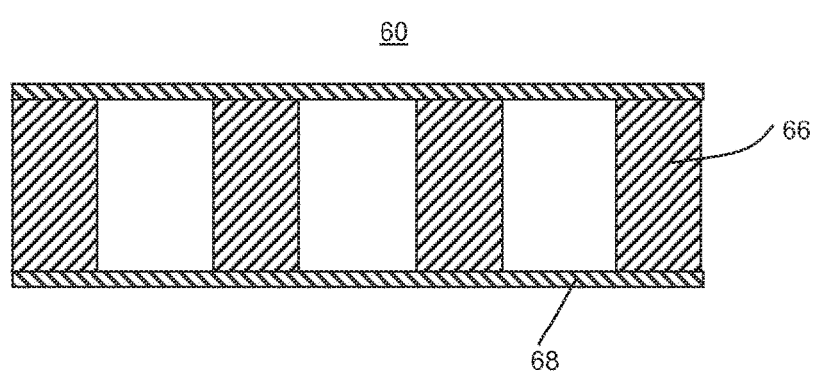
FIG. 20 is a cross-sectional view of the stent-graft of FIG. 19 taken along the 20-20 axis.

In another embodiment of the present invention, a stent-graft 60 is depicted in FIGS. 19 and 20. Stent graft 60 is a hollow tubular device having opposed open ends 62, 64. A graft 68 is supported by stent members 66. The stent members 66 may include any of the above-described shape memory polymeric materials. The stent members 66 may include a plurality of spaced-apart members as depicted in FIG. 20. As depicted in FIGS. 19 and 20, the stent members 66 may be in the shape of a hollow cylindrical portion. The present invention, however, is not so limited and other shape may be suitably used. For example, the stent members 66 may be in the shape of a ring or any other suitable shape or shapes. The graft 68 may also include any of the above-described shape memory polymeric materials or may be a different material, such as silicone, polyolefin or other polymeric material. The graft 68 may be secured to the stent members 66 by any suitable means, such as by the use of thermal, mechanical and/or chemical bonding.

Although the stent-graft 60 is depicted in FIGS. 19 and 20 as being fully covered by the graft 68, the present invention is not so limited. The stent-graft 60 may be fully covered or partially covered, i.e., having portions of the stent members 66 not covered by graft 68.

In further detail, suitable materials for the graft 68 may include elastic or polymeric materials, including, silicone, biodegradable materials, non-biodegradable materials, shape memory materials. Further, the graft 68 may be a coating on the stent members 66. The graft 68 may be may be in the form of a tubular structure, for example composed of polymeric material and/or silicone. The graft 68 may also comprise any plastic or polymeric material, desirably a somewhat hard but flexible plastic or polymeric material. The graft 68 may be transparent or translucent, desirably substantially or partially transparent. Furthermore, the graft 68 may be constructed of any suitable biocompatible materials, such as, but not limited to, polymers and polymeric materials, including fillers such as metals, carbon fibers, glass fibers or ceramics. Useful covering and/or lining materials include, but are not limited, polyethylene, polypropylene, polyvinyl chloride, polytetrafluoroethylene, including expanded polytetrafluoroethylene (ePTFE), fluorinated ethylene propylene, fluorinated ethylene propylene, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polyimides, polycarbonates, polyaldehydes, polyether ether ketone, natural rubbers, polyester copolymers, silicone, styrene-butadiene copolymers, polyethers, such as fully or partially halogenated polyethers, and copolymers and combinations thereof.

The stent members 66 may include any of the above-described grooves or may be free of such grooves. Further, either or both of the opposed ends 62, 64 may be flat or substantially flat as depicted in FIG. 19. Alternatively, either of both of the opposed ends 62, 64 may be rounded ends as described above.

Figure 21:
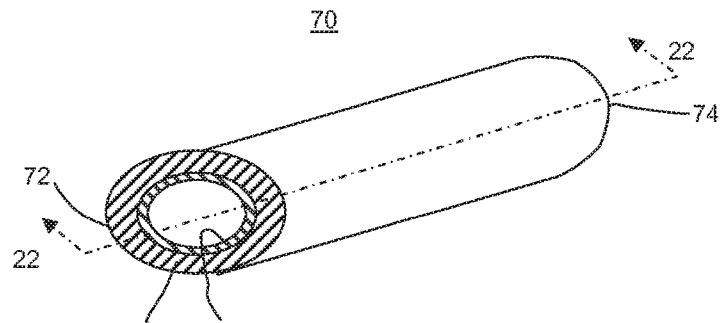
FIG. 21 depicts another embodiment of a stent-graft according to the present invention.
Figure 22A:
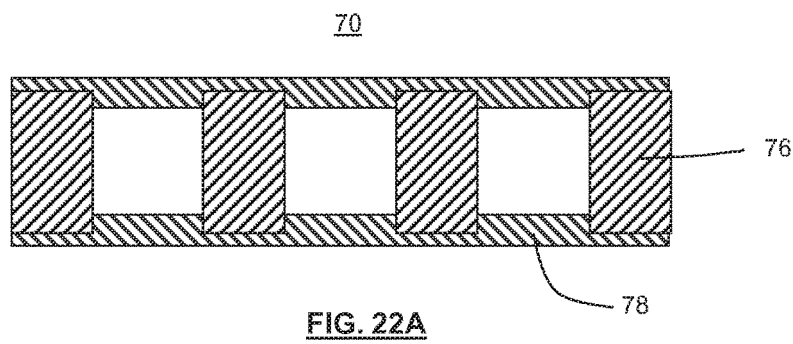
FIGS. 22A and 22B are cross-sectional views of the stent-graft of FIG. 21 taken along the 22-22 axis.
Figure 22B:
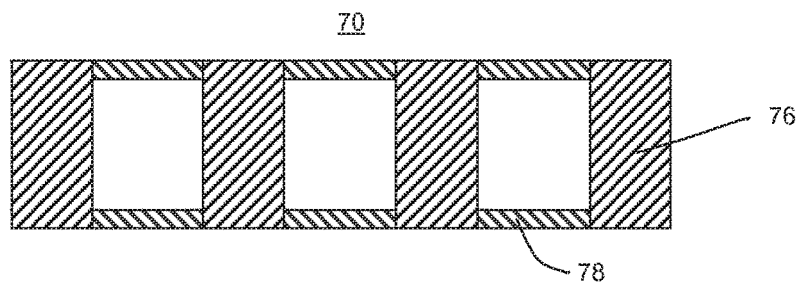

FIGS. 21-22B depict additional embodiments of stent-graft 70 according to the present invention. As depicted in FIG. 21, stent graft 70 is a hollow tubular device having opposed open ends 72, 74. The plurality of spaced apart stent members 76 may be embedded in the graft 78 as depicted in FIG. 22A to so engage the spaced apart stent members 76. Alternatively, the graft 78 may be disposed between the spaced apart stent members 76 as depicted in FIG. 22B to so engage the spaced apart stent members 76. The stent members 76 may include any of the above-described shape memory polymeric materials and may include any of the above-described grooves or be free of grooves. The graft 78 may also include any of the above-described shape memory polymeric materials or above-described graft materials. The graft 78 may also be secured to the stent members 76 by any suitable means, such as by the use of thermal, mechanical and/or chemical bonding. Although the stent-graft 70 is depicted in FIGS. 21 and 22A as being fully covered by the graft 78, the present invention is not so limited. The stent-graft 70 may be fully covered or partially covered, i.e., having portions of the stent members 76 not covered by graft 78.

Figure 23:
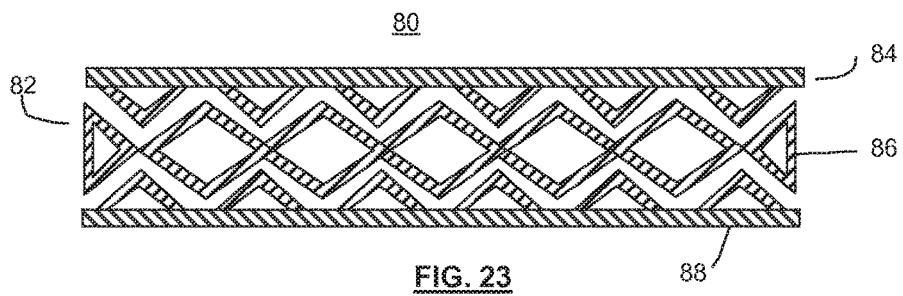
FIG. 23 depicts yet another embodiment of a stent-graft according to the present invention.

Stent-grafts of the present invention, however, are not limited to a plurality of spaced apart stent members 66, 76. For example, as depicted in FIG. 23, a slotted stent 86 of shape memory polymeric materials may be used to support graft 88. The slotted stent 86 depicted in FIG. 23 is in its radially expanded state where the "slots" of the unexpanded stent have been altered to an expanded "diamond" shape. The present invention is not limited to the use of a slotted stent 86 and any suitable stent configuration may be used. The slotted stent 86, or any suitable or similar stent configuration, may include an open lattice wall structure as depicted in FIG. 23. Included within the scope of an open lattice wall structure are the spaced apart stent members 66, 76 of FIGS. 20, 22A and 22B.

Stent 10, 10', 10", 10''' and/or stent-graft 60, 70, 80 may be treated with a therapeutic agent or agents. "Therapeutic agents", "pharmaceuticals," "pharmaceutically active agents", "drugs" and other related terms may be used interchangeably herein and include genetic therapeutic agents, non-genetic therapeutic agents and cells. Therapeutic agents may be used singly or in combination. A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition).

Non-limiting examples of useful therapeutic agents include, but are not limited to, adrenergic agents, adrenocortical steroids, adrenocortical suppressants, alcohol deterrents, aldosterone antagonists, amino acids and proteins, ammonia detoxicants, anabolic agents, analeptic agents, analgesic agents, androgenic agents, anesthetic agents, anorectic compounds, anorexic agents, antagonists, anterior pituitary activators and suppressants, anthelmintic agents, anti-adrenergic agents, anti-allergic agents, anti-amebic agents, anti-androgen agents, anti-anemic agents, anti-anginal agents, anti-anxiety agents, anti-arthritic agents, anti-asthmatic agents, anti-atherosclerotic agents, antibacterial agents, anticholelithic agents, anticholelithogenic agents, anticholinergic agents, anticoagulants, anticoccidal agents, anticonvulsants, antidepressants, antidiabetic agents, antidiuretics, antidotes, antidyskinetics agents, anti-emetic agents, anti-epileptic agents, anti-estrogen agents, antifibrinolytic agents, antifungal agents, antiglaucoma agents, antihemophilic agents, antihemophilic Factor, antihemorrhagic agents, antihistaminic agents, antihyperlipidemic agents, antihyperlipoproteinemic agents, antihypertensives, antihypotensives, anti-infective agents, anti-inflammatory agents, antikeratinizing agents, antimicrobial agents, antimigraine agents, antimitotic agents, antimycotic agents, antineoplastic agents, anti-cancer supplementary potentiating agents, antineutropenic agents, antiobsessional agents, antiparasitic agents, antiparkinsonian drugs, antipneumocystic agents, antiproliferative agents, antiprostatic hypertrophy drugs, antiprotozoal agents, antipruritics, antipsoriatic agents, antipsychotics, antirheumatic agents, antischistosomal agents, antiseborrheic agents, antispasmodic agents, antithrombotic agents, antitussive agents, anti-ulcerative agents, anti-urolithic agents, antiviral agents, benign prostatic hyperplasia therapy agents, blood glucose regulators, bone resorption inhibitors, bronchodilators, carbonic anhydrase inhibitors, cardiac depressants, cardioprotectants, cardiotonic agents, cardiovascular agents, choleretic agents, cholinergic agents, cholinergic agonists, cholinesterase deactivators, coccidiostat agents, cognition adjuvants and cognition enhancers, depressants, diagnostic aids, diuretics, dopaminergic agents, ectoparasiticides, emetic agents, enzyme inhibitors, estrogens, fibrinolytic agents, free oxygen radical scavengers, gastrointestinal motility agents, glucocorticoids, gonad-stimulating principles, hemostatic agents, histamine H2 receptor antagonists, hormones, hypocholesterolemic agents, hypoglycemic agents, hypolipidemic agents, hypotensive agents, HMGCoA reductase inhibitors, immunizing agents, immunomodulators, immunoregulators, immunostimulants, immunosuppressants, impotence therapy adjuncts, keratolytic agents, LHRH agonists, luteolysin agents, mucolytics, mucosal protective agents, mydriatic agents, nasal decongestants, neuroleptic agents, neuromuscular blocking agents, neuroprotective agents, NMDA antagonists, non-hormonal sterol derivatives, oxytocic agents, plasminogen activators, platelet activating factor antagonists, platelet aggregation inhibitors, post-stroke and post-head trauma treatments, progestins, prostaglandins, prostate growth inhibitors, prothyrotropin agents, psychotropic agents, radioactive agents, repartitioning agents, scabicides, sclerosing agents, sedatives, sedative-hypnotic agents, selective adenosine A1 antagonists, adenosine A2 receptor antagonists (e.g., CGS 21680, regadenoson, UK 432097 or GW 328267), serotonin antagonists, serotonin inhibitors, serotonin receptor antagonists, steroids, stimulants, thyroid hormones, thyroid inhibitors, thyromimetic agents, tranquilizers, unstable angina agents, uricosuric agents, vasoconstrictors, vasodilators, vulnerary agents, wound healing agents, xanthine oxidase inhibitors, and the like, and combinations thereof.

Useful non-genetic therapeutic agents for use in connection with the present invention include, but are not limited to, (a) anti-thrombotic agents such as heparin, heparin derivatives, urokinase, clopidogrel, and PPack (dextrophenylalanine proline arginine chloromethylketone);

(b) anti-inflammatory agents such as dexamethasone, prednisolone, corticosterone, budesonide, estrogen, sulfasalazine and mesalamine;

(c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors;

(d) anesthetic agents such as lidocaine, bupivacaine and ropivacaine;

(e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides;

(f) vascular cell growth promoters such as growth factors, transcriptional activators, and translational promotors;

(g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

(h) protein kinase and tyrosine kinase inhibitors (e.g., tyrphostins, genistein, quinoxalines);

(i) prostacyclin analogs;

(j) cholesterol-lowering agents;

(k) angiopoietins;

(l) antimicrobial agents such as triclosan, cephalosporins, aminoglycosides and nitrofurantoin;

(m) cytotoxic agents, cytostatic agents and cell proliferation affectors;

(n) vasodilating agents;

(o) agents that interfere with endogenous vasoactive mechanisms;

(p) inhibitors of leukocyte recruitment, such as monoclonal antibodies;

(q) cytokines;

(r) hormones;

(s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin;

(t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, diclomine);

(u) bARKct inhibitors;

(v) phospholamban inhibitors;

(w) Serca 2 gene/protein;

(x) immune response modifiers including aminoquizolines, for instance, imidazoquinolines such as resiquimod and imiquimod;

(y) human apolioproteins (e.g., AI, AII, AIII, AIV, AV, etc.);

(z) selective estrogen receptor modulators (SERMs) such as raloxifene, lasofoxifene, arzoxifene, miproxifene, ospemifene, PKS 3741, MF 101 and SR 16234;

(aa) PPAR agonists, including PPAR-alpha, gamma and delta agonists, such as rosiglitazone, pioglitazone, netoglitazone, fenofibrate, bexaotene, metaglidasen, rivoglitazone and tesaglitazar;

(bb) prostaglandin E agonists, including PGE2 agonists, such as alprostadil or ONO 8815Ly;

(cc) thrombin receptor activating peptide (TRAP);

(dd) vasopeptidase inhibitors including benazepril, fosinopril, lisinopril, quinapril, ramipril, imidapril, delapril, moexipril and spirapril;

(ee) thymosin beta 4;

(ff) phospholipids including phosphorylcholine, phosphatidylinositol and phosphatidylcholine; and (gg) VLA-4 antagonists and VCAM-1 antagonists.

The non-genetic therapeutic agents may be used individually or in combination, including in combination with any of the agents described herein.

Further examples of non-genetic therapeutic agents, not necessarily exclusive of those listed above, include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Useful genetic therapeutic agents for use in connection with the present invention include, but are not limited to, anti-sense DNA and RNA as well as DNA coding for the various proteins (as well as the proteins themselves), such as (a) anti-sense RNA; (b) tRNA or rRNA to replace defective or deficient endogenous molecules; (c) angiogenic and other factors including growth factors such as acidic and basic fibroblast growth factors, vascular endothelial growth factor, endothelial mitogenic growth factors, epidermal growth factor, transforming growth factor .alpha. and .beta., platelet-derived endothelial growth factor, platelet-derived growth factor, tumor necrosis factor .alpha., hepatocyte growth factor and insulin-like growth factor; (d) cell cycle inhibitors including CD inhibitors, and (e) thymidine kinase ("TK") and other agents useful for interfering with cell proliferation. DNA encoding for the family of bone morphogenic proteins ("BMP's") are also useful and include, but not limited to, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently desirably BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include, but not limited to, viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP), SP1017 (SUPRATEK), lipids such as cationic lipids, liposomes, lipoplexes, nanoparticles, or microparticles, with and without targeting sequences such as the protein transduction domain (PTD).

Cells for use in connection with the present invention may include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis (antirestenotics). Such agents are useful for the practice of the present invention and include one or more of the following:

(a) Ca-channel blockers including benzothiazapines such as diltiazem and clentiazem, dihydropyridines such as nifedipine, amlodipine and nicardapine, and phenylalkylamines such as verapamil;

(b) serotonin pathway modulators including: 5-HT antagonists such as ketanserin and naftidrofuryl, as well as 5-HT uptake inhibitors such as fluoxetine;

(c) cyclic nucleotide pathway agents including phosphodiesterase inhibitors such as cilostazole and dipyridamole, adenylate/Guanylate cyclase stimulants such as forskolin, as well as adenosine analogs;

(d) catecholamine modulators including α-antagonists such as prazosin and bunazosine, β-antagonists such as propranolol and α/β-antagonists such as labetalol and carvedilol;

(e) endothelin receptor antagonists such as bosentan, sitaxsentan sodium, atrasentan, endonentan;

(f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine;

(g) Angiotensin Converting Enzyme (ACE) inhibitors such as cilazapril, fosinopril and enalapril;

(h) ATII-receptor antagonists such as saralasin and losartin;

(i) platelet adhesion inhibitors such as albumin and polyethylene oxide;

(j) platelet aggregation inhibitors including cilostazole, aspirin and thienopyridine (ticlopidine, clopidogrel) and GP IIb/IIIa inhibitors such as abciximab, epitifibatide and tirofiban;

(k) coagulation pathway modulators including heparinoids such as heparin, low molecular weight heparin, dextran sulfate and .beta.-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C;

(l) cyclooxygenase pathway inhibitors such as aspirin, ibuprofen, flurbiprofen, indomethacin and sulfinpyrazone;

(m) natural and synthetic corticosteroids such as dexamethasone, prednisolone, methprednisolone and hydrocortisone;

(n) lipoxygenase pathway inhibitors such as nordihydroguairetic acid and caffeic acid;

(o) leukotriene receptor antagonists;

(p) antagonists of E- and P-selectins;

(q) inhibitors of VCAM-1 and ICAM-1 interactions;

(r) prostaglandins and analogs thereof including prostaglandins such as PGE1 and PGI2 and prostacyclin analogs such as ciprostene, epoprostenol, carbacyclin, iloprost and beraprost;

(s) macrophage activation preventers including bisphosphonates;

(t) HMG-CoA reductase inhibitors such as lovastatin, pravastatin, atorvastatin, fluvastatin, simvastatin and cerivastatin;

(u) fish oils and omega-3-fatty acids;

(v) free-radical scavengers/antioxidants such as probucol, vitamins C and E, ebselen, trans-retinoic acid, SOD (orgotein) and SOD mimics, verteporfin, rostaporfin, AGI 1067, and M 40419;

(w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives;

(x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518;

(y) cell motility inhibitors such as cytochalasin B;

(z) antiproliferative/antineoplastic agents including antimetabolites such as purine antagonists/analogs (e.g., 6-mercaptopurine and pro-drugs of 6-mercaptopurine such as azathioprine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), olimus family drugs (e.g., sirolimus, everolimus, tacrolimus, zotarolimus, etc.), cerivastatin, flavopiridol and suramin;

(aa) matrix deposition/organization pathway inhibitors such as halofuginone or other quinazolinone derivatives, pirfenidone and tranilast;

(bb) endothelialization facilitators such as VEGF and RGD peptide;

(cc) blood rheology modulators such as pentoxifylline and (dd) glucose cross-link breakers such as alagebrium chloride (ALT-711).

These therapeutic agents may be used individually or in combination, including in combination with any of the agents described herein.

Numerous additional therapeutic agents useful for the practice of the present invention are also disclosed in U.S. Pat. No. 5,733,925 to Kunz, the contents of which is incorporated herein by reference.

A wide range of therapeutic agent loadings may used in connection with the dosage forms of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth. The stent 10, 10', 10", 10''' may include coatings, linings, layers, laminates, agent delivery particles, reinforcement particles, reinforcement strands.

The following embodiments or aspects of the invention may be combined in any fashion and combination and be within the scope of the present invention, as follows:

Embodiment 1

An implantable, radially distensible device comprising: a tubular structure having an open first end and an opposed open second end, the tubular structure having a wall between said first open end and said second end to define an open lumen therethrough, the wall having an outer surface and an opposed inner surface defining a wall thickness therebetween; the wall comprising a shape memory polymeric material; wherein the tubular structure is a self-supporting wall structure.

Embodiment 2

The device of embodiment 1, wherein the tubular structure has a substantially solid wall and has a plurality of grooves disposed within the outer surface of said wall.

Embodiment 3

The device of embodiment 1, wherein the device is radially distensible between a radially contracted state and a radially expanded state.

Embodiment 4

The device of embodiment 1, wherein the self-supporting wall structure does not have an open lattice wall structure.

Embodiment 5

The device of embodiment 1, wherein the self-supporting wall structure is a substantially solid wall without gaps in a radially expanded state.

Embodiment 6

The device of embodiment 2, wherein the grooves are present in the wall when the device is in a radially expanded state.

Embodiment 7

The device of embodiment 2, wherein the grooves are present in the wall when the device is in a radially contracted state and in a radially expanded state.

Embodiment 8

The device of embodiment 2, wherein the grooves are selected from the group consisting of a semicircular groove, a truncated circular groove, a semicircular groove with rounded surfaces, a groove having a flat bottom portion and smoothly rounded sides, a triangular-shaped groove, a groove having a flat bottom portion and sloped sides, a square-shaped groove, a rectangular-shaped groove, and combinations thereof.

Embodiment 9

The device of embodiment 2, wherein the grooves are a plurality of radially orientated grooves.

Embodiment 10

The device of embodiment 2, wherein the grooves are a plurality of helically orientated grooves.

Embodiment 11

The device of embodiment 2, wherein the grooves are a plurality of interconnected helically orientated grooves having a first helical pattern and a second helical pattern.

Embodiment 12

The device of embodiment 11, wherein the grooves are crisscrossed helical grooves.

Embodiment 13

The device of embodiment 2, wherein the grooves are interconnected grooves.

Embodiment 14

The device of embodiment 1, wherein the shape memory polymeric material of the wall of the device comprises shape memory polymeric polycyclooctene.

Embodiment 15

The device of embodiment 1, wherein the shape memory polymeric material of the wall of the device further includes a radiopaque material.

Embodiment 16

The device of embodiment 1, wherein the shape memory polymeric material is biodegradable.

Embodiment 17

The device of embodiment 1, wherein the wall thickness is from about 0.038 cm to about 0.635 cm.

Embodiment 18

The device of embodiment 2, wherein the grooves comprise a depth and wherein the depth the grooves are from about 5% to about 50% of the wall thickness Embodiment 19

The device of embodiment 1, wherein device comprises a longitudinal length between the first open end and the second open end and wherein the longitudinal length of the device is from about 1 cm to about 15 cm.

Embodiment 20

The device of embodiment 2, wherein device comprises a longitudinal length between the first open end and the second open end and wherein adjacently juxtaposed grooves are disposed at a distance from about 0.25 cm to about 3 cm from one and the other along the longitudinal length of the device.

Embodiment 21

The device of embodiment 1, wherein device is a stent

Embodiment 22

The device of embodiment 1, further comprising: at least two tubular structures and a graft disposed over the at least two tubular structures, wherein the at least two tubular structures are spaced apart from one and the other.

Embodiment 23

The device of embodiment 1, further comprising: at least two tubular structures and a graft disposed between the at least two tubular structures, wherein the at least two tubular structures are spaced apart from one and the other.

Embodiment 24

The device of embodiment 1, further comprising: at least two tubular structures and a graft; wherein the at least two tubular structures are embedded in the graft and, wherein the at least two tubular structures are spaced apart from one and the other.

Embodiment 25

The device of embodiment 1, wherein the tubular structure is an open lattice wall structure.

Embodiment 26

The device of embodiment 25, further comprising tubular structure further comprising a graft disposed over the open lattice wall structure.

Embodiment 27

The device of embodiment 25, wherein the open lattice wall structure is a stent.

Embodiment 28

A method of making a stent, comprising: providing a shape memory polymer; forming the shape memory polymer into a tubular structure having an open first end and an opposed open second end, the tubular structure having a wall between said first open end and said second end to define an open lumen therethrough, the wall having an outer surface and an opposed inner surface defining a wall thickness therebetween.

Embodiment 29

The method of embodiment 28, further comprising: disposing grooves within the outer surface of the wall.

Embodiment 30

The method of embodiment 28, wherein the step of providing the shape memory polymer further comprises providing shape memory polymeric polycyclooctene.

Embodiment 31

The method of embodiment 28, wherein the step of forming the shape memory polymer into the tubular structure further comprises molding the shape memory polymer.

Embodiment 32

The method of embodiment 28, wherein the step of forming the shape memory polymer into the tubular structure further comprises casting the shape memory polymer.

Embodiment 33

The method of embodiment 28, wherein the step of forming the shape memory polymer into the tubular structure further comprises extruding the shape memory polymer.

Embodiment 34

The method of embodiment 29, wherein the step of disposing grooves within the outer surface of the wall further comprises mechanically forming the grooves.

Embodiment 35

The method of embodiment 34, wherein the step of mechanically forming the grooves further comprises milling the outer surface of the wall, grinding the outer surface of the wall, cutting the outer surface of the wall, laser cutting the outer surface of the wall, etching the outer surface of the wall, masking the outer surface of the wall, or removal of a sacrificial layer or filament from the outer surface of the wall to form the grooves.

Embodiment 36

The method of embodiment 31, further comprising molding the grooves within the outer surface of the wall.

Embodiment 37

An assembly for intraluminal delivery of a stent, comprising: a delivery device having an elongate tube; and a radially distensible stent comprising: a tubular structure having an open first end and an opposed open second end, the tubular structure having a wall between said first open end and said second end to define an open lumen therethrough, the wall having an outer surface and an opposed inner surface defining a wall thickness therebetween; the wall comprising a shape memory polymeric material; and grooves disposed within the outer surface of said wall; wherein the stent is disposed in a contracted state on the elongate tube of the delivery device.

Embodiment 38

The assembly of embodiment 37, wherein the delivery device further comprises an expandable member.

Embodiment 39

The assembly of embodiment 37, wherein the delivery device further comprises a heat source.

Embodiment 40

A method for intraluminal delivery of a stent, comprising providing an assembly, comprising: a delivery device having an elongate tube; and a radially distensible stent comprising: a tubular structure having an open first end and an opposed open second end, the tubular structure having a wall between said first open end and said second end to define an open lumen therethrough, the wall having an outer surface and an opposed inner surface defining a wall thickness therebetween; the wall comprising a shape memory polymeric material; and grooves disposed within the outer surface of said wall; wherein the stent is disposed in a contracted state on the elongate tube of the delivery device; advancing the assembly to a site within a bodily lumen; radially expanding the stent within the bodily lumen; and withdrawing the delivery device to leave the stent within the bodily lumen.

Embodiment 41

The method of embodiment 40, wherein the step of radially expanding the stent within the bodily lumen further comprises supplying heat from a heat source to the stent to radially expand the stent.

Embodiment 42

The method of embodiment 40, wherein the step of radially expanding the stent within the bodily lumen further comprises providing an expandable member to mechanically radially expand the stent.

Embodiment 43

The method of embodiment 41, further comprising: providing an expandable member to mechanically expand the stent.

Embodiment 44

Use of the device of embodiments 1-27

Embodiment 45

A stent made by the method of embodiment 28-36

Embodiment 46

Use of the assembly of embodiments 37-39

While various embodiments of the present invention are specifically illustrated and/or described herein, it will be appreciated that modifications and variations of the present invention may be effected by those skilled in the art without departing from the spirit and intended scope of the invention. Further, any of the embodiments or aspects of the invention as described in the claims or throughout the specification may be used with one and another without limitation.

What is claimed is:

1. An implantable, radially distensible device comprising:
a solid tubular structure having an outer circumference, an open first end and an opposed open second end and an open lumen extending therebetween, the solid tubular structure including a plurality of tubular structures and a graft, the plurality of tubular structures being spaced apart and unconnected from one another, wherein the graft is secured to the plurality of tubular structures and extends between and radially beyond the plurality of tubular structures, the graft having a continuous wall extending around an entire outer circumference of the tubular structures and between the first end and the second end, the wall having an outer surface and an opposed inner surface defining a wall thickness therebetween, the wall comprising a shape memory polymeric material, wherein the inner surface is in contact with outer surfaces of the plurality of tubular structures.

2. The device of claim 1, wherein the plurality of tubular structures are hollow cylinders.

3. The device of claim 2, wherein the hollow cylinders are partially embedded in the graft.

4. The device of claim 2, wherein the graft includes a plurality of graft portions disposed between the spaced apart tubular structures.

5. The device of claim 1, wherein the graft completely covers the tubular structure.

6. The device of claim 1, wherein the tubular structure has a plurality of grooves disposed within the outer surface of the wall.

7. The device of claim 6, wherein the outer surface of the wall between the plurality of grooves extends parallel to a longitudinal axis of the tubular structure.

8. The device of claim 7, wherein a length of the outer surface of the wall between two adjacent grooves is greater than a width of the grooves extending along the longitudinal axis.

9. The device of claim 6, wherein the grooves are present in the wall when the device is in a radially contracted state and in a radially expanded state.

10. The device of claim 6, wherein the grooves are selected from the group consisting of a semicircular groove, a truncated circular groove, a semicircular groove with rounded surfaces, a groove having a flat bottom portion and smoothly rounded sides, a triangular-shaped groove, a groove having a flat bottom portion and sloped sides, a square-shaped groove, a rectangular-shaped groove, and combinations thereof.

11. The device of claim 6, wherein the grooves are a plurality of radially or helically orientated grooves.

12. The device of claim 11, wherein the grooves are a plurality of interconnected helically orientated grooves having a first helical pattern and a second helical pattern.

13. The device of claim 6, wherein the grooves are interconnected grooves.

14. The device of claim 6, wherein the grooves comprise a depth and wherein the depth the grooves are from about 5% to about 50% of the wall thickness.

15. The device of claim 1, wherein the tubular structure has one or more slots extending through the wall.

16. The device of claim 1, wherein adjacent spaced apart tubular structures are connected to each other by the graft alone.

17. An implantable, radially distensible device comprising:
a plurality of hollow cylindrical tubular structures spaced apart from one another, each tubular structure of the plurality of hollow cylindrical tubular structures formed of a shape memory polymeric material and comprising:
an outer circumference;
an open first end;
an opposed open second end;
a continuous wall extending around the entire outer circumference and between the first end and the second end to define an open lumen therethrough; and
a wall thickness measured between an outer surface of the wall and an opposed inner surface of the wall; and
a graft surrounding the plurality of hollow cylindrical tubular structures and extending between and separating adjacent ones of the plurality of spaced apart hollow cylindrical tubular structures, wherein adjacent spaced apart hollow cylindrical tubular structures are connected to each other by the graft alone.

18. The device of claim 17, wherein the plurality of hollow cylindrical tubular structures are each partially embedded in the graft.

19. An implantable, radially distensible device comprising:
- a plurality of solid tubular structures, each solid tubular structure having an outer circumference, an open first end and an opposed open second end, the tubular structure having a solid wall extending around the entire outer circumference of the solid tubular structure and between the first end and the second end to define an open lumen therethrough, the wall having an outer surface and an opposed inner surface, the entire wall being free of gaps and comprising a shape memory polymeric material, wherein the tubular structure is a self-supporting wall structure;
- a plurality of grooves disposed in the outer surface of the wall, wherein the grooves are present in the wall when the device is in a radially contracted state and in a radially expanded state; and
- a graft secured to the outer surface of each of the tubular structures and extending therebetween.

20. The device of claim 19, wherein the outer surface of the wall between the plurality of grooves extends parallel to a longitudinal axis of the tubular structure.

* * * * *